United States Patent
Aronov et al.

(10) Patent No.: US 7,501,415 B2
(45) Date of Patent: Mar. 10, 2009

(54) SELECTIVE INHIBITORS OF ERK PROTEIN KINASE AND USES THEREOF

(75) Inventors: Alexander Aronov, Watertown, MA (US); Michael Hale, Bedford, MA (US); Francois Maltais, Tewksbury, MA (US); Gabriel Martinez-Botella, West Roxbury, MA (US); Judith Straub, Santa Cruz, CA (US); Qing Tang, Acton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 294 days.

(21) Appl. No.: 11/312,618

(22) Filed: Dec. 20, 2005

(65) Prior Publication Data

US 2006/0160807 A1   Jul. 20, 2006

Related U.S. Application Data

(60) Provisional application No. 60/638,502, filed on Dec. 23, 2004.

(51) Int. Cl.
*C07D 403/04* (2006.01)
*A61K 31/506* (2006.01)

(52) U.S. Cl. .............. 514/241; 514/242; 514/255.05; 514/275; 544/182; 544/212; 544/295; 544/296; 544/330; 544/331

(58) Field of Classification Search .......... 544/182, 544/212, 295, 296, 330, 331; 514/242, 255.05, 514/275, 241
See application file for complete search history.

(56) References Cited

U.S. PATENT DOCUMENTS 6,743,791 B2 * 6/2004 Cao et al. ............... 514/235.8
7,244,735 B2 * 7/2007 Straub et al. ........... 514/252.14

FOREIGN PATENT DOCUMENTS

WO   02/064586    8/2002
WO   2004/083203  9/2004

OTHER PUBLICATIONS

Damasio, Alzheimer's Disease and Related Dementias, Cecil Textbook of Medicine, 20th Edition, vol. 2, pp. 1992-1996, 1996.*
Simone, Oncology: Introduction, Cecil Textbook of Medicine, 20th Edition, vol. 1, pp. 1004-1010, 1996.*
Douglas, Jr. Introduction to Viral Diseases, Cecil Textbook of Medicine, 20th Edition, vol. 2, pp. 1739-1747, 1996.*
Layzer, Degenerative Diseases of the Nervous System, Cecil Textbook of Medicine, 20th Edition, vol. 2, pp. 2050-2057, 1996.*

* cited by examiner

*Primary Examiner*—Deepak Rao
(74) *Attorney, Agent, or Firm*—Daniel A. Pearson

(57) ABSTRACT

Described herein are compounds that are useful as ERK2 inhibitors. These compounds, and pharmaceutically acceptable compositions thereof, are useful for treating or lessening the severity of a variety of disorders, including proliferative disorders such as cancer.

7 Claims, No Drawings

SELECTIVE INHIBITORS OF ERK PROTEIN KINASE AND USES THEREOF

CROSS-REFERENCE TO RELATED APPLICATIONS

This application claims the benefit of U.S. Provisional Application No. 60/638,502, filed Dec. 23, 2004, which is hereby incorporated by reference in its entirety.

BACKGROUND OF THE INVENTION

The present invention relates to heteroaryl compounds that are protein kinase inhibitors, compositions containing such compounds, and methods for their use. The compounds and compositions of the invention are useful for treating cancer, neurological disorders, autoimmune disorders, and other diseases that are alleviated by protein kinase inhibitors.

Mammalian cells respond to extracellular stimuli by activating signaling cascades that are mediated by members of the mitogen-activated protein (MAP) kinase family, which include the extracellular signal regulated kinases (ERKs), the p38 MAP kinases and the c-Jun N-terminal kinases (JNKs). MAP kinases (MAPKs) are activated by a variety of signals including growth factors, cytokines, UV radiation, and stress-inducing agents. MAPKs are serine/threonine kinases and their activation occur by dual phosphorylation of threonine and tyrosine at the Thr-X-Tyr segment in the activation loop. MAPKs phosphorylate various substrates including transcription factors, which in turn regulate the expression of specific sets of genes and thus mediate a specific response to the stimulus.

ERK2 is a widely distributed protein kinase that achieves maximum activity when both Thr183 and Tyr185 are phosphorylated by the upstream MAP kinase, MEK1. Upon activation, ERK2 phosphorylates many regulatory proteins, including the protein kinases Rsk90 and MAPKAP2, and transcription factors such as ATF2, Elk-1, c-Fos, and c-Myc. ERK2 is also a downstream target of the Ras/Raf dependent pathways and relays the signals from these potentially oncogenic proteins. ERK2 has been shown to play a role in the negative growth control of breast cancer cells and hyperexpression of ERK2 in human breast cancer has been reported. Activated ERK2 has also been implicated in the proliferation of endothelin-stimulated airway smooth muscle cells, suggesting a role for this kinase in asthma.

Overexpression of receptor tyrosine kinases such as EGFR and ErbB2, as well as activating mutations in the Ras GTPase proteins or B-Raf mutants are major contributors to human cancer. These genetic alterations are correlated with poor clinical prognosis and result in activation of the Raf-1/2/3-MEK1/2-ERK1/2 signal transduction cascade in a broad panel of human tumors. Activated ERK (i.e., ERK1 and/or ERK2) is a central signaling molecule that has been associated with the control of proliferation, differentiation, anchorage-independent cell survival, and angiogenesis, contributing to a number of processes that are important for the formation and progression of malignant tumors. These data suggest that an ERK1/2 inhibitor will exert pleiotropic activity, including proapoptotic, anti-proliferative, anti-metastatic and anti-angiogenic effects, and offer a therapeutic opportunity against a very broad panel of human tumors.

Many diseases are associated with abnormal cellular responses triggered by protein kinase-mediated events, such as, for example, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents and there is still a need for new therapeutic agents that inhibit these protein targets.

SUMMARY OF THE INVENTION

It has been surprisingly found that compounds of this invention, and compositions thereof, are effective as selective inhibitors of ERK2. These compounds have the general formulae I and II:

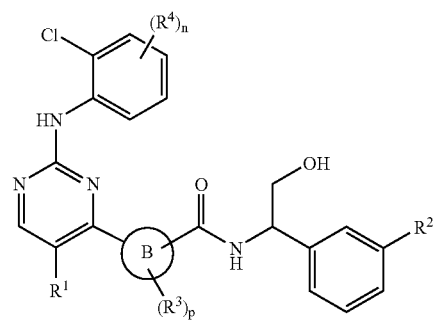

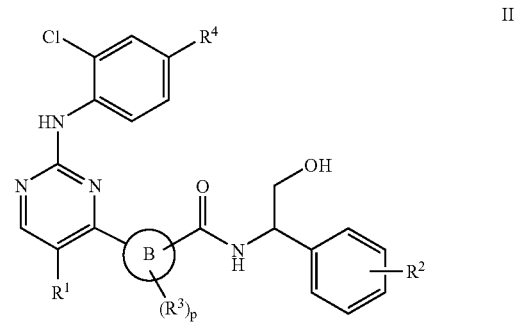

or a pharmaceutically acceptable salt thereof, wherein Ring B, n, p, $R^1$, $R^2$, $R^3$, and $R^4$ are as defined herein.

These compounds and pharmaceutically acceptable compositions thereof are useful for treating or lessening the severity of a variety of disorders, especially proliferative disorders such as cancer.

DETAILED DESCRIPTION OF THE INVENTION

Compounds of the Invention

In a first aspect, the present invention features a compound having the formula:

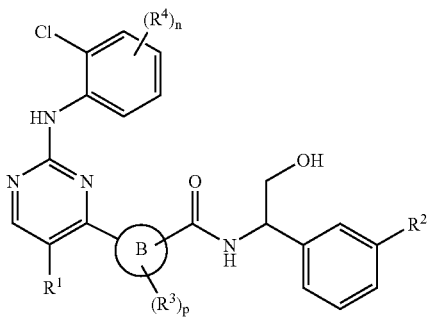

or a pharmaceutically acceptable salt thereof, where:
Ring B is selected from the group consisting of:

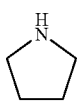 a

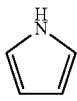 b

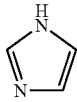 c

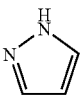 d

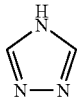 e

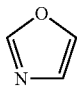 f

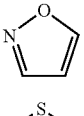 g

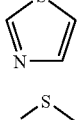 h

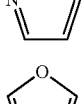 i

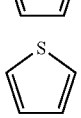 j k

 l

 m

 n

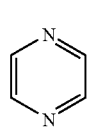 o

 p

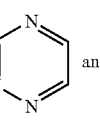 and q

 r $R^1$ is CN, halogen, $N(R)_2$, OR, or R;
n is 0-4;
each R is independently selected from hydrogen or an optionally substituted $C_{1-6}$ aliphatic group, or two R on the same nitrogen are taken together with the nitrogen to form a 5-8 membered heterocyclyl or heteroaryl ring having 1-3 heteroatoms independently selected from nitrogen, oxygen, or sulfur;
$R^2$ is R, halogen, $(CH_2)_wOR$, $CO_2R$, $(CH_2)_wN(R)_2$, $(CH_2)_wSR$, NRC(O)R, $NRC(O)N(R)_2$, $C(O)N(R)_2$, $SO_2R$, $NRSO_2R$, C(O)R, CN, or $SO_2N(R)_2$;
each w is 0-3;
each $R^3$ is independently selected from oxo, $NO_2$, R, F, Cl, $N(R)_2$, OR, SR, NRC(O)R, $NRC(O)N(R)_2$, $C(O)N(R)_2$, $SO_2R$, $NRSO_2R$, C(O)R, CN, $SO_2N(R)_2$, N(R)O, ON(R), or N(R)N(R);
p is 0-2; and
each $R^4$ is independently selected from oxo, $NO_2$, R, F, Cl, $N(R)_2$, OR, SR, NRC(O)R, $NRC(O)N(R)_2$, $C(O)N(R)_2$, $SO_2R$, $NRSO_2R$, C(O)R, CN, $SO_2N(R)_2$, N(R)O, ON(R), or N(R)N(R); and
provided that when n and p are both zero, Ring B is pyrrol-3-yl, and $R^1$ is methyl, then $R^2$ is not $CF_3$.

As used herein, the following definitions shall apply unless otherwise indicated. As described herein, compounds or classes of compounds of the invention may optionally be substituted with one or more substituents, such as, for example, one, two, three, four, or five substituents. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, this term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, this term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups. If a substituent radical or structure is not identified or defined as "optionally substituted," the substituent radical or structure is unsubstituted.

The term "aliphatic" or "aliphatic group," as used herein, means a straight-chain or branched $C_1$-$C_{12}$ hydrocarbon chain that is completely saturated or that contains one or more units of unsaturation, or a monocyclic $C_3$-$C_8$ hydrocarbon or bicyclic $C_8$-$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in the bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

Each of the terms "alkyl," "alkoxy," "hydroxyalkyl," "alkoxyalkyl," and "alkoxycarbonyl," used alone or as part of a larger moiety, includes both straight and branched chains containing one to twelve carbon atoms. The terms "alkenyl" and "alkynyl" used alone or as part of a larger moiety shall include both straight and branched chains containing two to twelve carbon atoms.

The term "haloalkyl," "haloalkenyl," or "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "aryl" used alone or as part of a larger moiety as in "aralkyl," "aralkoxy," or "aryloxyalkyl," refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring."

The term "heterocycle," "heterocyclyl," or "heterocyclic," as used herein, means non-aromatic, monocyclic, bicyclic or tricyclic ring systems having five to fourteen ring members in which one or more ring members is a heteroatom, wherein each ring in the system contains 3 to 7 ring members.

The term "heteroaryl," used alone or as part of a larger moiety as in "heteroaralkyl" or "heteroarylalkoxy," refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic."

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group are selected from halogen, —$R^o$, —$OR^o$, —$SR^o$, 1,2-methylenedioxy, 1,2-ethylenedioxy, protected OH (such as acyloxy, which is recognized in the art as —OC(O)$R^o$), phenyl (Ph), Ph substituted with $R^o$, —O(Ph), O-(Ph) substituted with $R^o$, —$CH_2$(Ph), —$CH_2$(Ph) substituted with $R^o$, —$CH_2CH_2$(Ph), —$CH_2CH_2$(Ph) substituted with $R^o$, —$NO_2$, —CN, —N($R^o$)$_2$, —$NR^o$C(O)$R^o$, —$NR^o$C(O)N($R^o$)$_2$, —$NR^o$CO$_2R^o$, —$NR^o$N$R^o$C(O)$R^o$, —$NR^o$N$R^o$C(O)N($R^o$)$_2$, —$NR^o$N$R^o$CO$_2R^o$, —C(O)C(O)$R^o$, —C(O)$CH_2$C(O)$R^o$, —$CO_2R^o$, —C(O)$R^o$, —C(O)N($R^o$)$_2$, —OC(O)N($R^o$)$_2$, —S(O)$_2R^o$, —$SO_2$N($R^o$)$_2$, —S(O)$R^o$, —$NR^o$SO$_2$N($R^o$)$_2$, —$NR^o$SO$_2R^o$, —C(=S)N($R^o$)$_2$, —C(=NH)—N($R^o$)$_2$, or —($CH_2$)$_y$NHC(O)$R^o$, where y is 0-6, wherein each $R^o$ is independently selected from hydrogen, an optionally substituted $C_{1-6}$ aliphatic, an unsubstituted 5-6 membered heteroaryl or heterocyclic ring, phenyl (Ph), —O(Ph), or —$CH_2$(Ph)-$CH_2$(Ph). Substituents on the aliphatic group of $R^o$ are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2$H, $CO_2$($C_{1-4}$ aliphatic), O(halo($C_{1-4}$ aliphatic)), or halo ($C_{1-4}$ aliphatic).

In addition, an aryl or heteroaryl group may contain one or more substituents selected from —CH=CH(Ph) optionally substituted with $R^o$; —$NR^o$C(S)N($R^o$)$_2$; —C(S)$R^o$; —B(O$R^o$)$_2$, —OC(O)$R^o$; —C(O)N(O$R^o$)$R^o$; —C(=NO$R^o$) $R^o$; —N(O$R^o$)$R^o$; -L'-$R^o$; -L'-N($R^o$)$_2$; -L'-$SR^o$; -L'-$OR^o$; -L'-($C_{3-10}$ cycloaliphatic), -L'-($C_{6-10}$ aryl), -L'-(5-10 membered heteroaryl), -L'-(5-10 membered heterocyclyl), oxo, $C_{1-4}$ haloalkoxy, $C_{1-4}$ haloalkyl, -L'-$NO_2$, -L'-CN, -L'-OH, -L'-$CF_3$; wherein L' is a $C_{1-6}$ alkylene group in which up to three methylene units are replaced by —NH—, —$NR^o$—, —O—, —S—, —$CO_2$—, —OC(O)—, —C(O)CO—, —C(O)—, —C(O)NH—, —C(O)$NR^o$—, —C(=N—CN)—, —NHCO—, —$NR^o$CO—, —NHC(O)O—, —$NR^o$C(O)O—, —$SO_2$NH—, —$SO_2NR^o$—, —NHSO$_2$—, —$NR^o$SO$_2$—, —NHC(O)NH—, —$NR^o$C(O)NH—, —NHC(O)$NR^o$—, —$NR^o$C(O)$NR^o$, —OC(O)NH—, —OC(O)$NR^o$—, —NHSO$_2$NH—, —$NR^o$SO$_2$NH—, —NHSO$_2$$NR^o$—, —$NR^o$SO$_2$$NR^o$—, —SO—, or —$SO_2$—, and wherein each occurrence of $R^o$ is independently selected from hydrogen, optionally substituted $C_{1-6}$ aliphatic, an unsubstituted 5- to 6-membered heteroaryl or heterocyclic ring, phenyl, or —$CH_2$(Ph), or, two independent occurrences of $R^o$, on the same substituent or different substituents, taken together with the atom(s) to which each $R^o$ group is bound, form a 5-8-membered heterocyclyl, aryl, or heteroaryl ring or a 3- to 8-membered cycloalkyl ring, wherein the heteroaryl or heterocyclyl ring has 1 to 3 heteroatoms independently selected from nitrogen, oxygen, or sulfur, wherein optional substituents on the aliphatic group of $R^o$ are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), $O(haloC_{1-4}$ aliphatic), or $haloC_{1-4}$ aliphatic, wherein each of the $C_{1-4}$ aliphatic groups of $R^o$ is unsubstituted.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR*, =NN(R*)$_2$, =NNHC(O)R*, =NNHCO$_2$(alkyl), =NNHSO$_2$(alkyl), or =NR*, wherein each R* is independently selected from hydrogen or an optionally substituted $C_{1-6}$ aliphatic, and where optional substituents on the aliphatic group of R* are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), $O(halo-C_{1-4}$ aliphatic), and halo ($C_{1-4}$ aliphatic), wherein each of the foregoing $C_{1-4}$ aliphatic groups of R* is unsubstituted.

Substituents on the nitrogen of a non-aromatic heterocyclic ring are selected from —$R^+$, —$N(R^+)_2$, —$C(O)R^+$, —$CO_2R^+$, —$C(O)C(O)R^+$, —$C(O)CH_2C(O)R^+$, —$SO_2R^+$, —$SO_2N(R^+)_2$, —$C(=S)N(R^+)_2$, —$C(=NH)$—$N(R^+)_2$, or —$NR^+SO_2R^+$; wherein $R^+$ is hydrogen, an optionally substituted $C_{1-6}$ aliphatic, optionally substituted phenyl (Ph), optionally substituted —O(Ph), optionally substituted —$CH_2$(Ph), optionally substituted —$CH_2CH_2$(Ph), or an unsubstituted 5-6 membered heteroaryl or heterocyclic ring. Substituents on the aliphatic group or the phenyl ring of $R^+$ are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), $O(halo(C_{1-4}$ aliphatic)), or halo ($C_{1-4}$ aliphatic).

The term "alkylidene chain" refers to a straight or branched carbon chain that may be fully saturated or have one or more units of unsaturation and has two points of connection to the rest of the molecule.

The compounds of this invention are limited to those that are chemically feasible and stable. The term "stable," as used herein, refers to compounds that are not substantially altered when subjected to conditions to allow for their production, detection, and, preferably, their recovery, purification, and use for one or more of the purposes disclosed herein. Therefore, a combination of substituents or variables in the compounds described above is permissible only if such a combination results in a stable or chemically feasible compound. In certain embodiments, a stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of hydrogen by a deuterium or tritium, or the replacement of a carbon by a $^{13}C$- or $^{14}C$-enriched carbon are within the scope of this invention.

Compounds of this invention may exist in alternative tautomeric forms. Unless otherwise indicated, the representation of either tautomer is meant to include the other.

The compounds of formula I are generically described in U.S. Pat. No. 6,743,791. It has been surprisingly found that 2-chloro substituent on the aniline group, depicted above, imparts selectivity for ERK2 protein kinase over other kinases. It has also been surprisingly found that the $R^2$ group, when $R^2$ is other than hydrogen, also imparts selectivity for ERK2 protein kinase.

In one embodiment, $R^1$ of a compound of formula I is selected from hydrogen, $N(R)_2$, halogen, OH, or an optionally substituted $C_{1-6}$ aliphatic. When $R^1$ is an optionally substituted aliphatic group, preferred substituents on the aliphatic group are $R^o$, halo, nitro, alkoxy, and amino. Examples of such $R^1$ groups include chloro, fluoro, methyl, ethyl, propyl, cyclopropyl, cyclohexyl, $CH_2OCH_3$, $CH_2OH$, $NH_2$, $NHCH_3$, NHAc, $NHC(O)NHCH_3$, and $CH_2NHCH_3$. In one example, the $R^1$ group of formula I is methyl. In another example, the $R^1$ group of formula I is hydrogen.

In another embodiment, the $R^2$ group of a compound of formula I is halogen, optionally substituted $C_{1-6}$ aliphatic, OR, or SR. Examples of such $R^2$ groups of formula I include chloro, fluoro, methyl, ethyl, isopropyl, $OCH_3$, OH, or $SCH_3$. In one example, the $R^2$ group of formula I is chloro. According to another example, the $R^2$ group of formula I is hydrogen. In some particular embodiments, the carbon that is bonded to the phenyl ring that bears $R^2$ has the (S)-configuration.

In certain embodiments, p is one and the $R^3$ substituent on the Ring B group of formula I is hydrogen, methyl, or ethyl. In other embodiments, p is 0.

In yet another embodiment, n is 1 and the $R^4$ group of formula I is halogen, $NO_2$, R, OR, or $N(R)_2$. Examples of such $R^4$ groups include fluoro, $NH_2$, Cl, Br, $OCH_3$, haloalkyl (e.g., $CF_3$), $OCF_3$, and OH. In a further embodiment, the $R^4$ group is fluoro or $NO_2$. In yet a further embodiment, the $R^4$ group of a compound of formula I is fluoro at the 4-position.

In certain embodiments, the Ring B group of a compound of formula I is a 5-membered ring selected from:

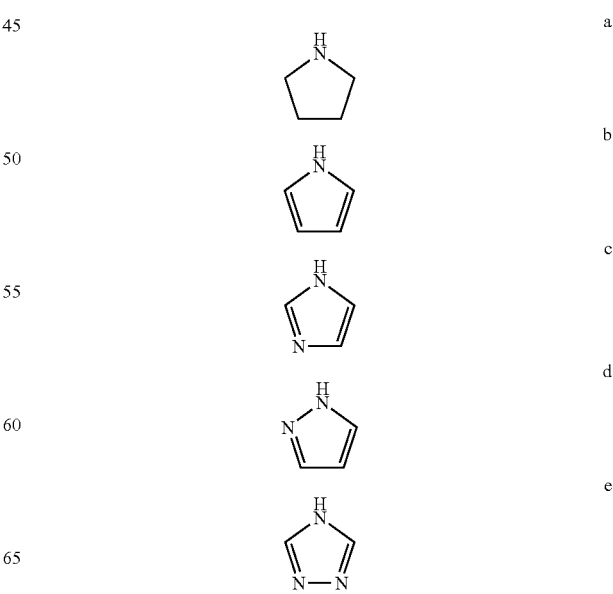

-continued
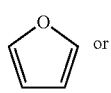 or
In other embodiments, the Ring B group of formula I is a 6-membered aryl ring selected from:
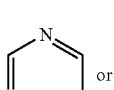 or
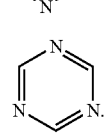
Representative ring systems of formula I are set forth in Table 2.
Table 2: Representative Ring Systems of Formula I
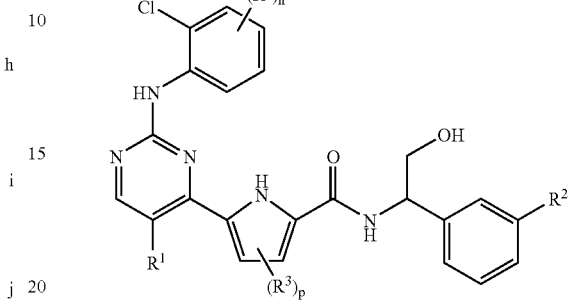
I-a
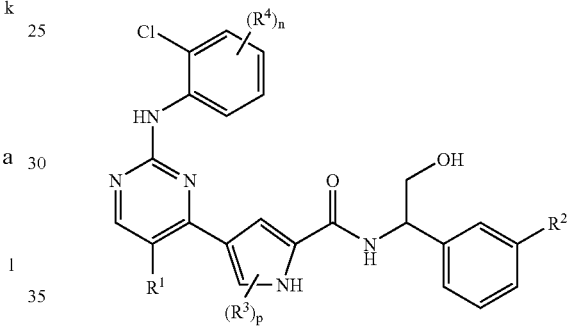
I-b
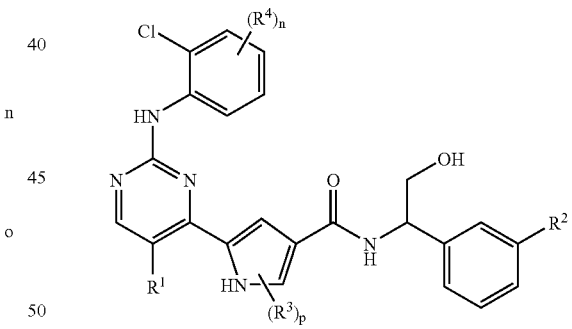
I-c
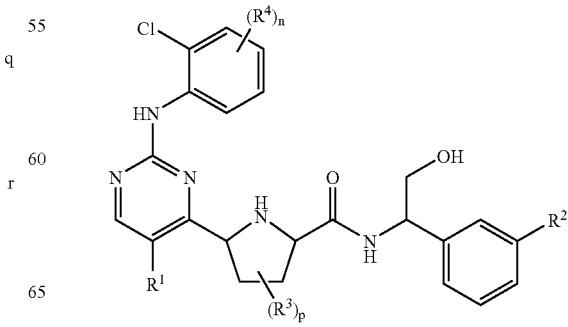
I-d

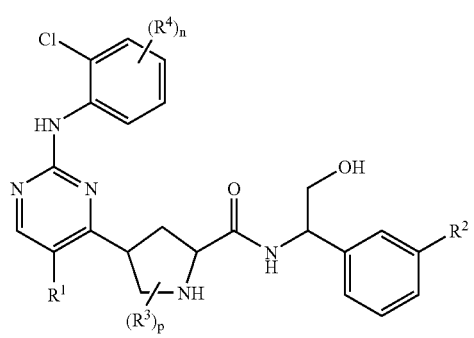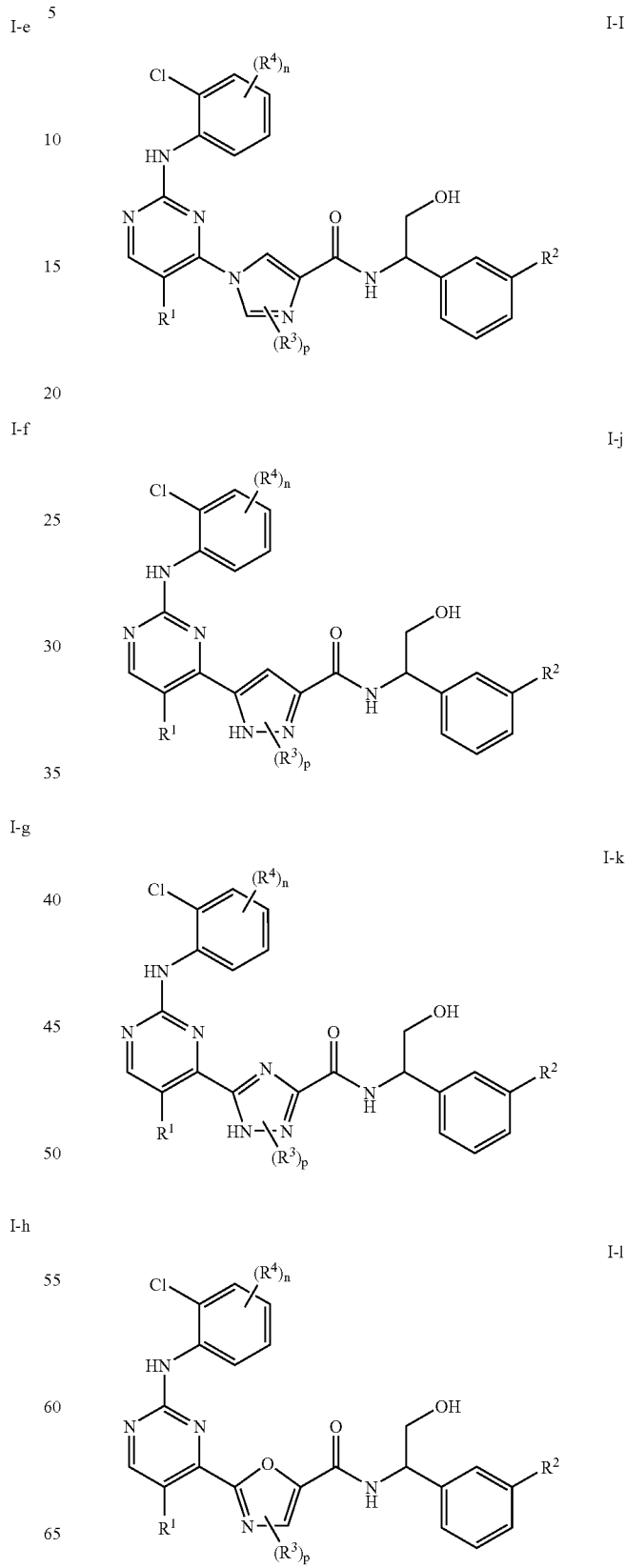

-continued
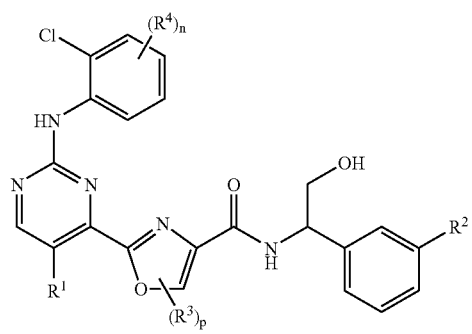
I-m
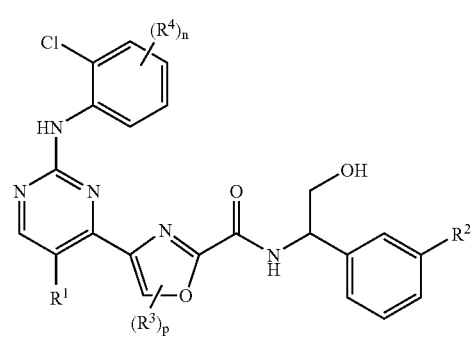
I-n
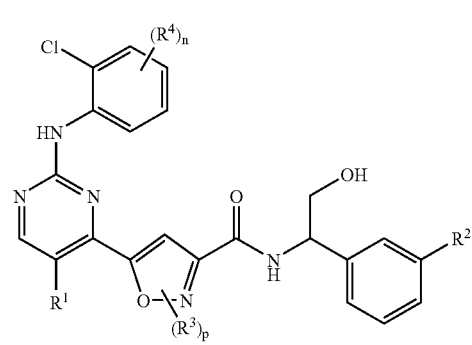
I-o
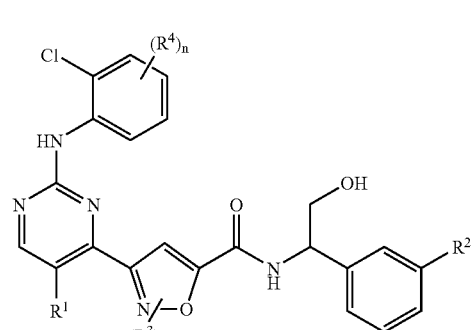
I-p
-continued
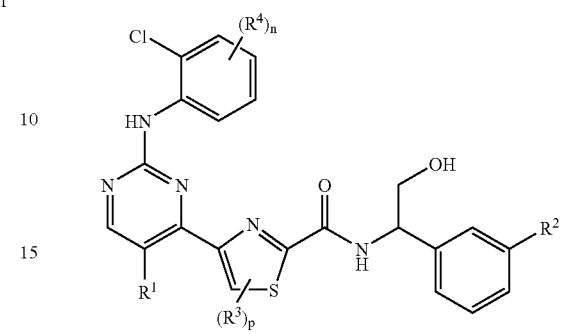
I-q
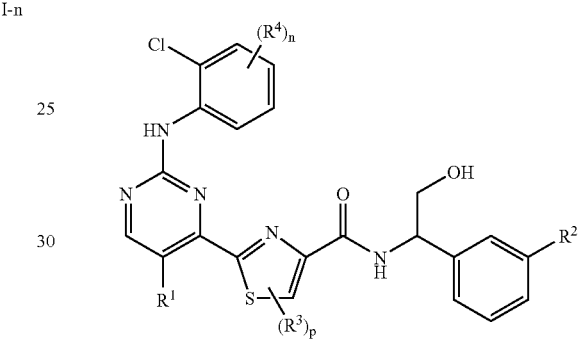
I-r
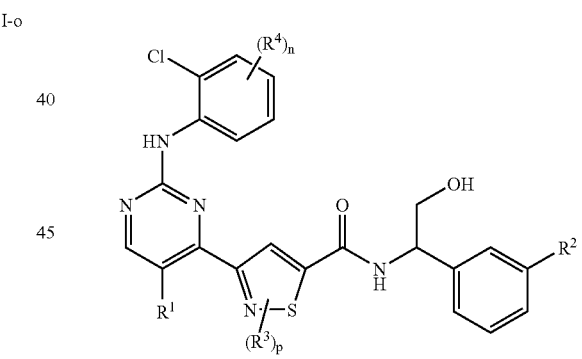
I-s
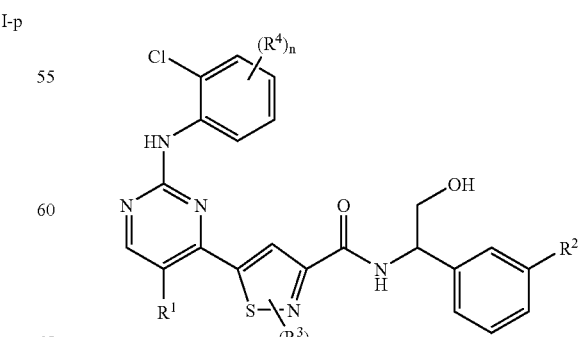
I-t -continued
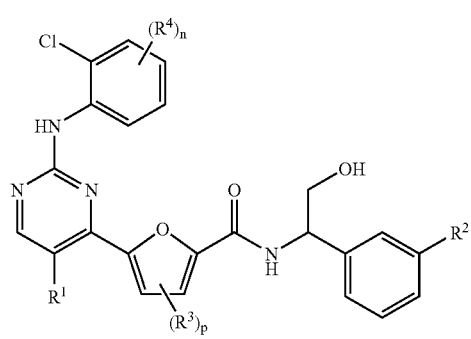
I-u
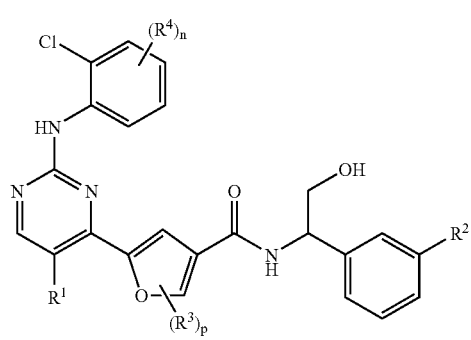
I-v
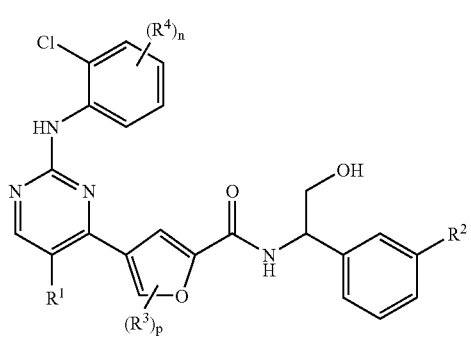
I-w
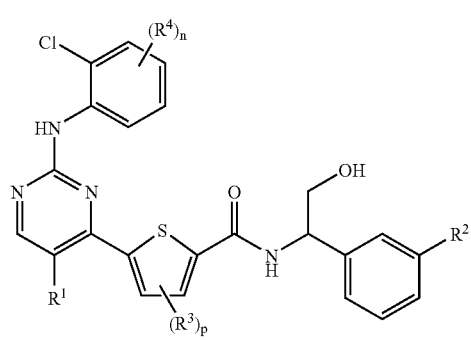
I-x
-continued
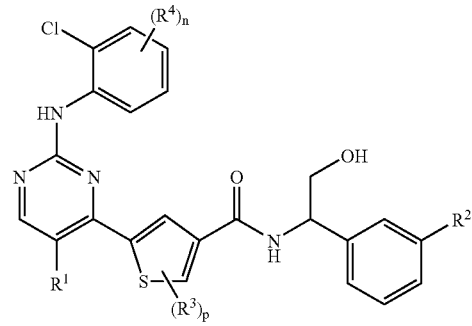
I-y
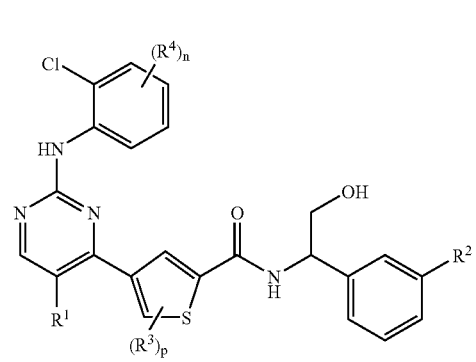
I-z
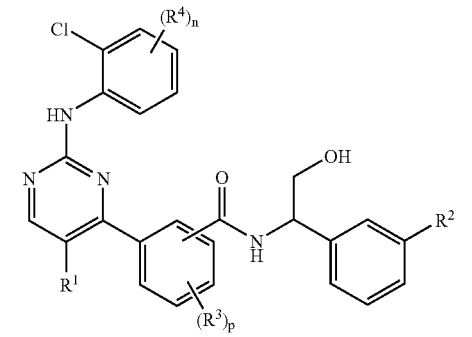
I-aa
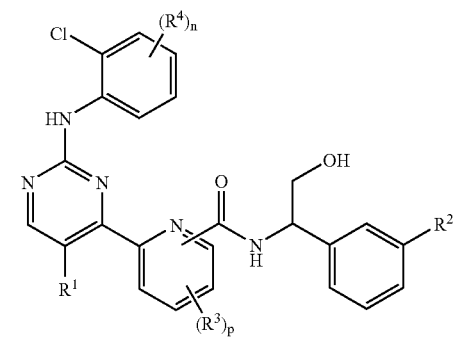
I-bb

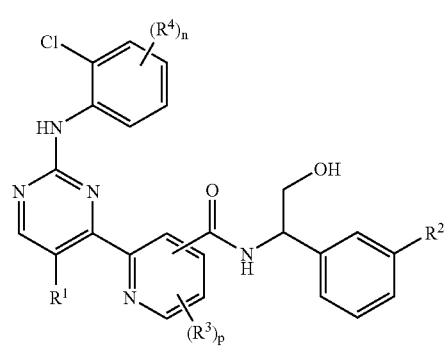
I-cc
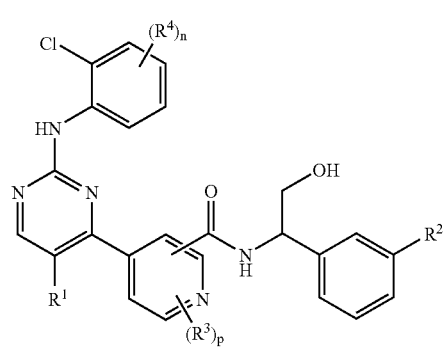
I-dd
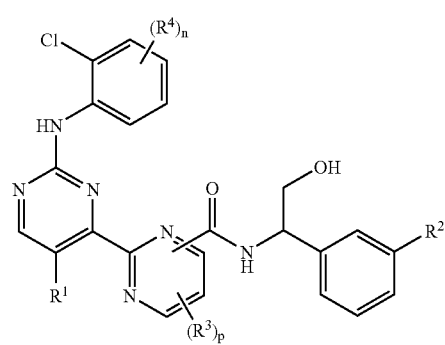
I-ee
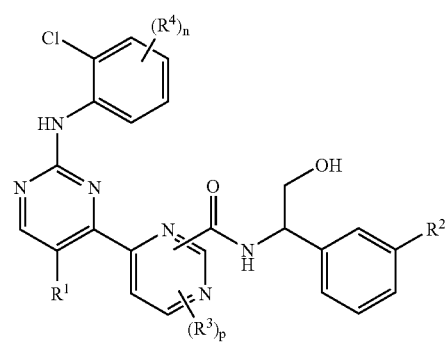
I-ff
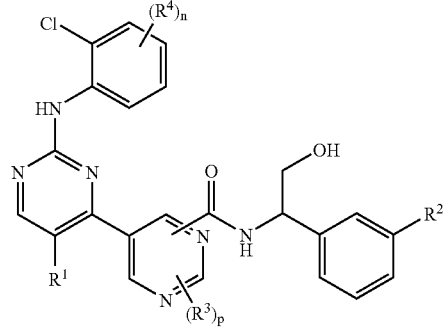
I-gg
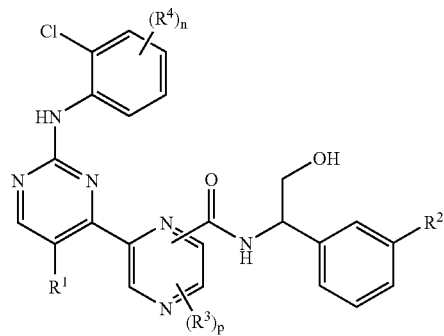
I-hh
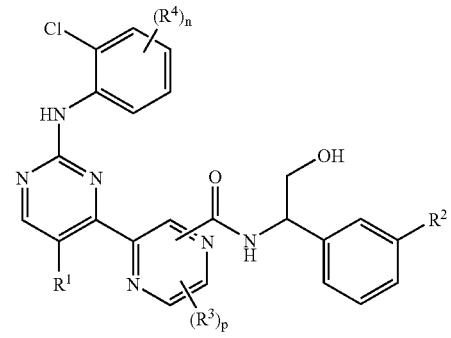
I-ii
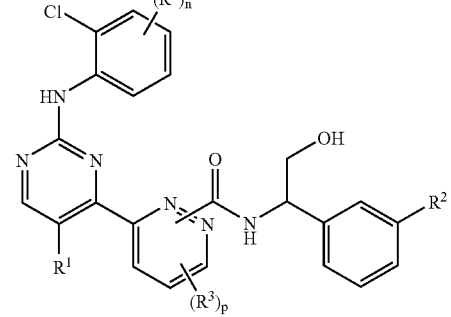
I-jj -continued
I-kk
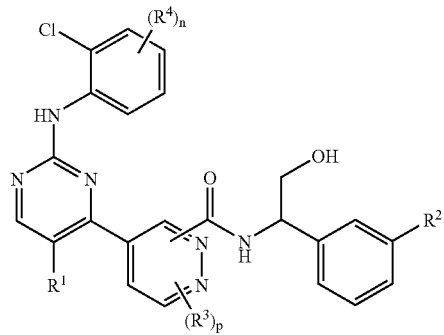
I-ll
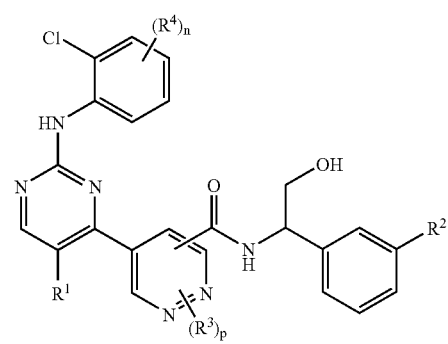
I-mm
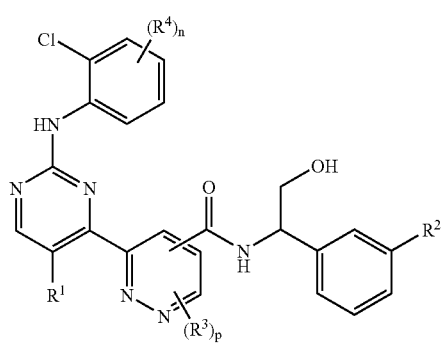
I-nn
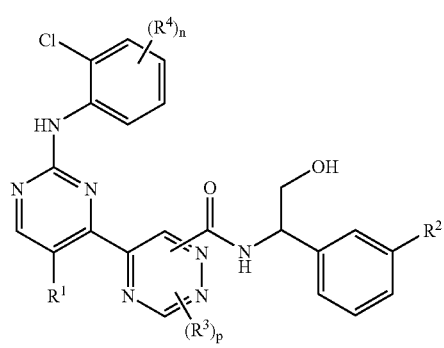
-continued
I-oo
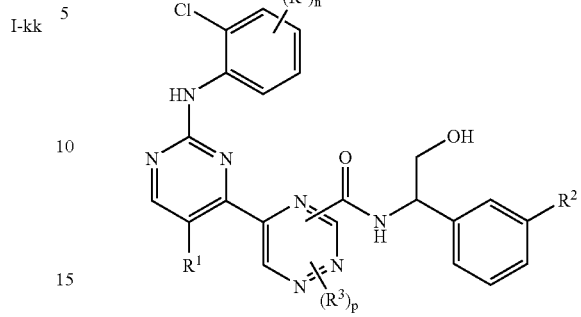
I-pp
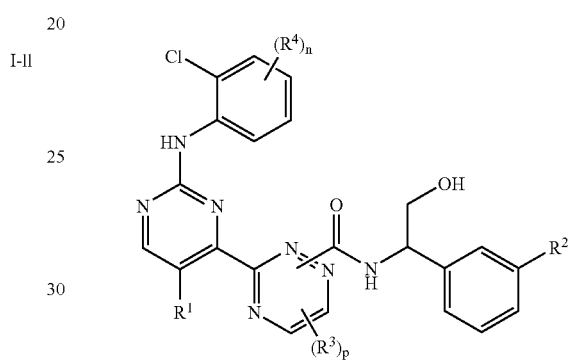
I-qq
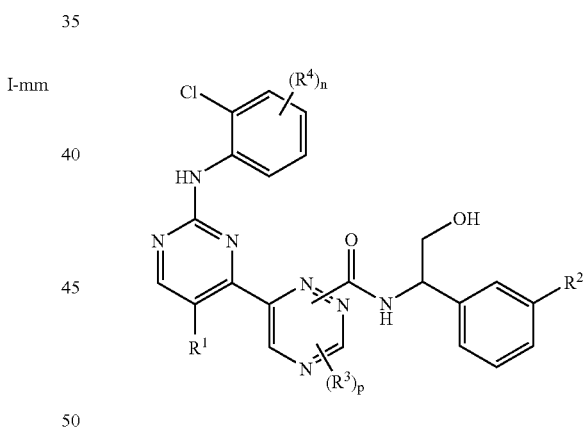
I-rr
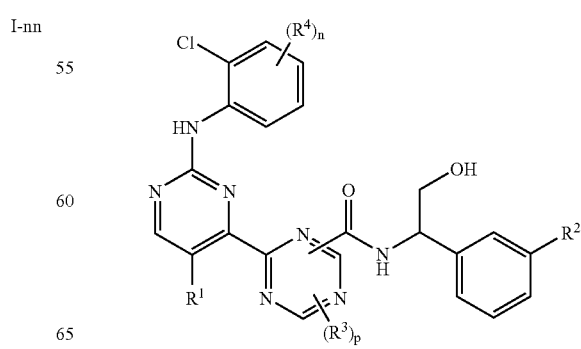

In another aspect, the invention features a compound having the formula:

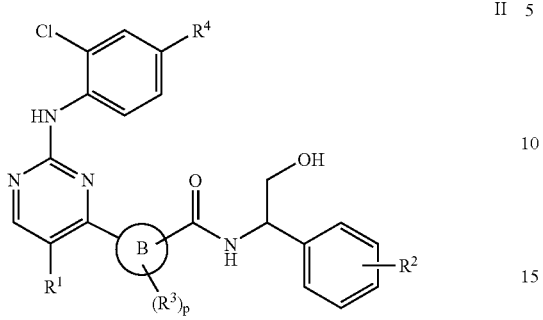

II or a pharmaceutically acceptable salt thereof, wherein Ring B, p, $R^1$, $R^2$, $R^3$, and $R^4$ are as defined above for a compound of formula I. These compounds are generically described in U.S. Pat. No. 6,743,791. It has been surprisingly found that 2-chloro substituent on the aniline group depicted above imparts selectivity for ERK2 protein kinase and that the $R^4$ substituent at the 4-position of the aniline group depicted above imparts metabolic stability to the compound as compared to compounds lacking an $R^4$ substituent at the 4-position of the aniline group.

In one embodiment, $R^1$ of a compound of formula II is selected from hydrogen, $N(R)_2$, halogen, OH, or an optionally substituted group selected from $C_{1-6}$ aliphatic. When $R^1$ is an optionally substituted aliphatic group, preferred substituents on the aliphatic group are $R^o$, halo, nitro, alkoxy, and amino. Examples of such $R^1$ groups include chloro, fluoro, methyl, ethyl, propyl, cyclopropyl, cyclohexyl, $CH_2OCH_3$, $CH_2OH$, $NH_2$, $NHCH_3$, NHAc, $NHC(O)NHCH_3$, and $CH_2NHCH_3$. In one example, the $R^1$ group of formula II is methyl. In another example, the $R^1$ group of formula II is hydrogen.

In certain embodiments, the $R^2$ group of formula II is halogen, optionally substituted $C_{1-6}$ aliphatic, OR, or SR. Examples of such $R^2$ groups of formula II include chloro, fluoro, methyl, ethyl, isopropyl, $OCH_3$, OH, or $SCH_3$. In a further embodiment, the $R^2$ group of formula II is chloro. In another further embodiment, the $R^2$ group of formula II is hydrogen. In yet another further embodiment, the carbon that is bonded to the phenyl ring that bears $R^2$ has the (S)-configuration.

In certain embodiments, p is one and the $R^3$ substituent on the Ring B group of formula II is hydrogen, methyl, or ethyl. In other embodiments, p is 0.

In another embodiment, the $R^4$ group of a compound of formula II is halogen, $NO_2$, R, OR, or $N(R)_2$. Examples of such $R^4$ groups include fluoro, $NH_2$, Cl, Br, $OCH_3$, haloalkyl (e.g., $CF_3$), $OCF_3$, and OH. In a further embodiment, $R^4$ is fluoro, chloro, or $NO_2$. In yet another further embodiment, the $R^4$ group of a compound of formula II is fluoro.

In certain embodiments, the Ring B group of formula II is a 5-membered ring selected from:

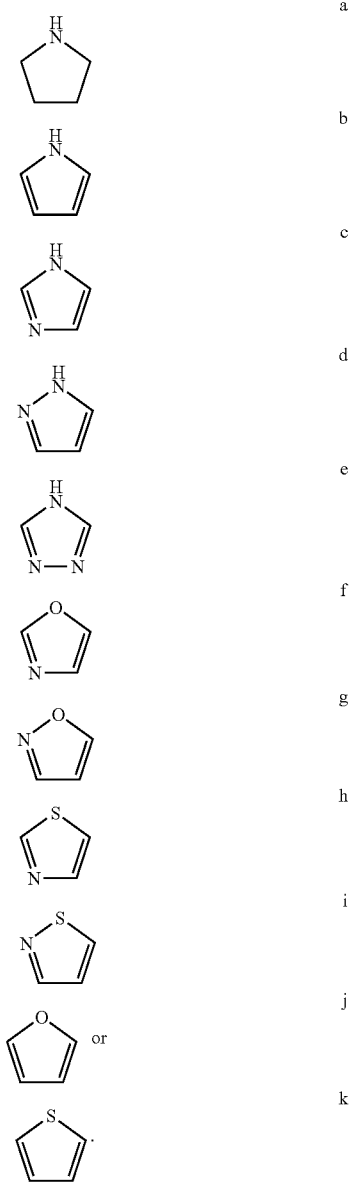

In other embodiments, the Ring B group of formula II is a 6-membered aryl ring selected from:

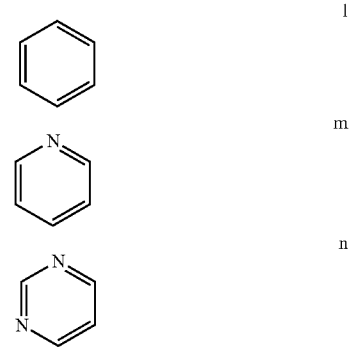

-continued
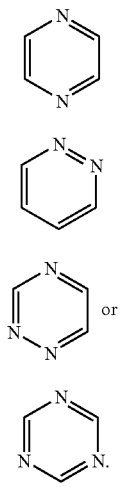
or
Representative ring systems of formula II are set forth below in Table 3.
Table 3: Representative Ring Systems of Formula II
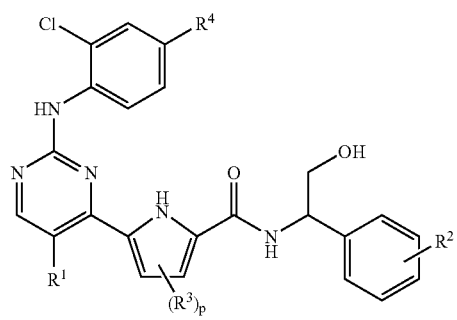
II-a
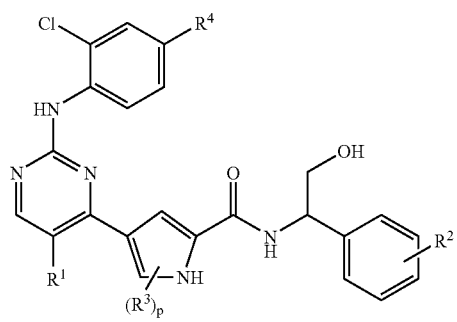
II-b
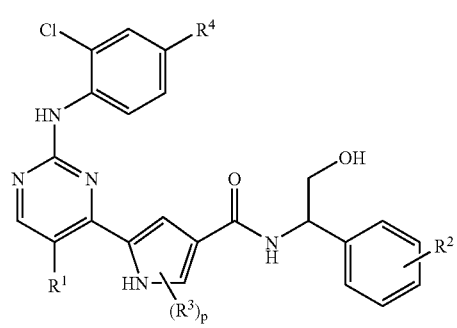
II-c
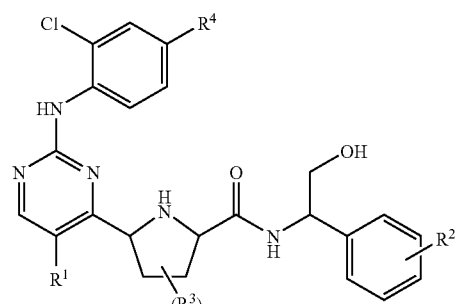
II-d
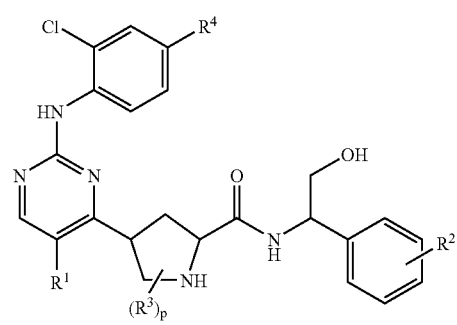
II-e
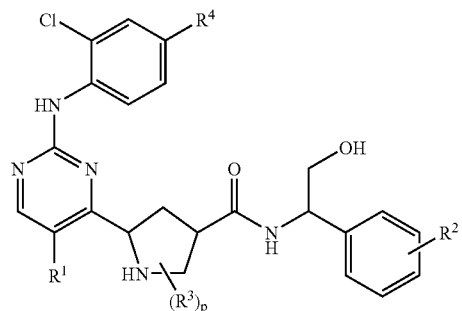
II-f
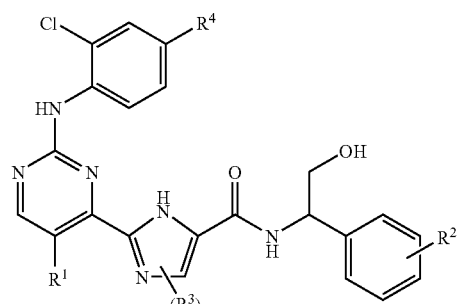
II-g
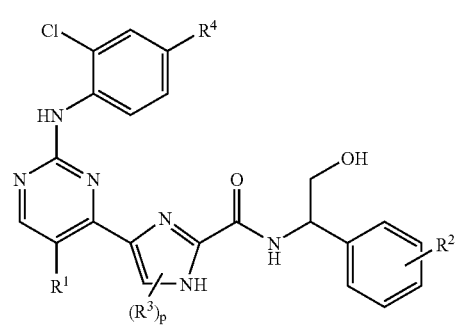
II-h -continued
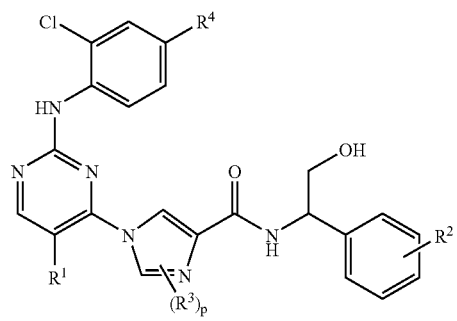 II-i
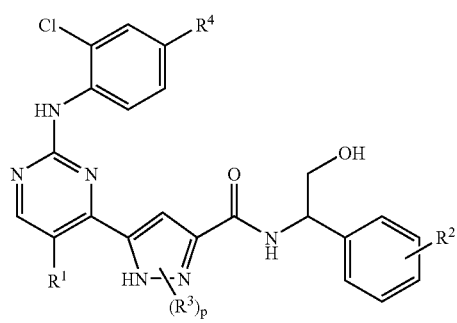 II-j
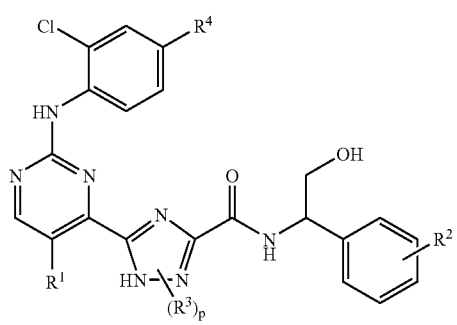 II-k
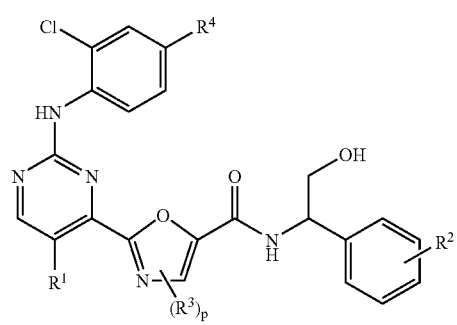 II-l
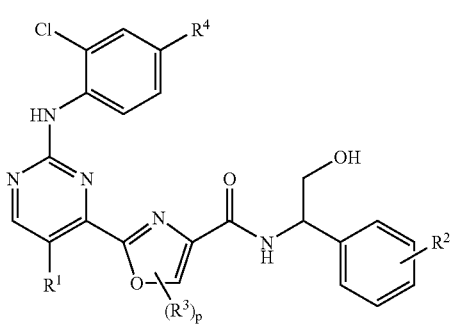 II-m
-continued
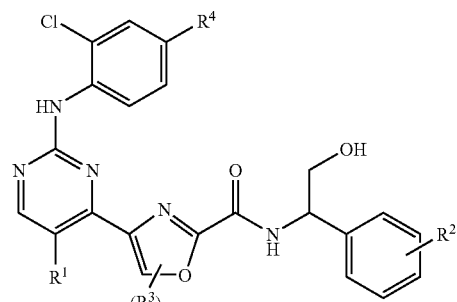 II-n
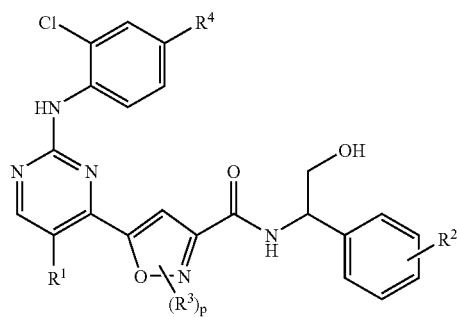 II-o
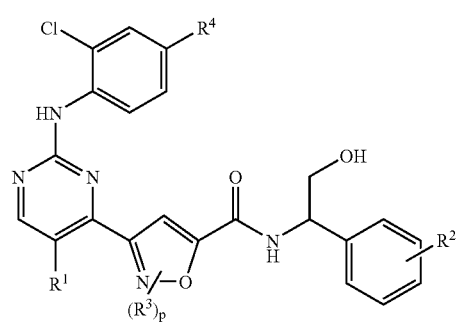 II-p
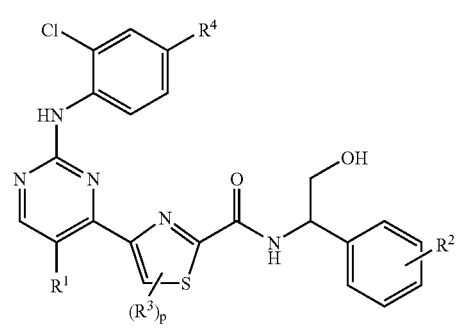 II-q
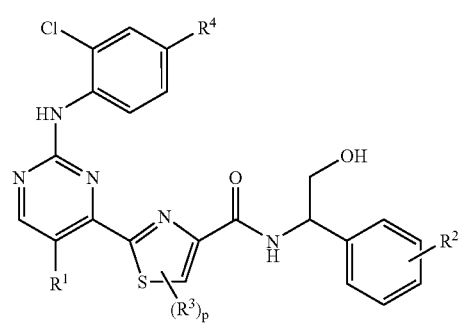 II-r

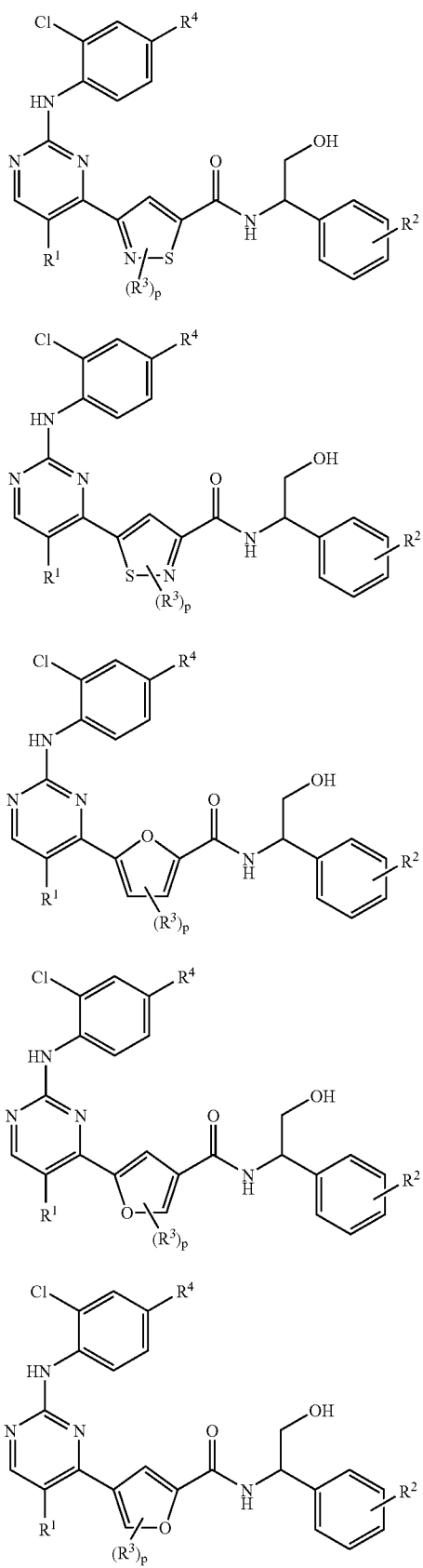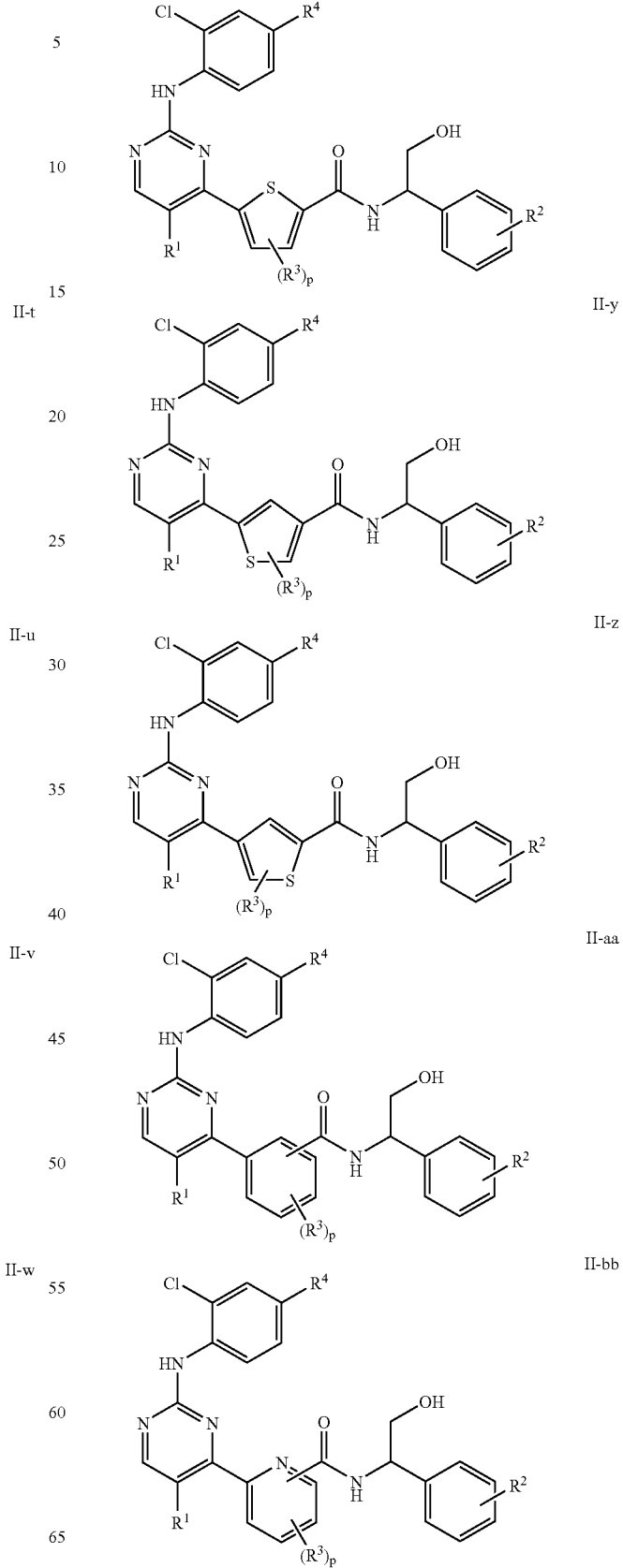

-continued
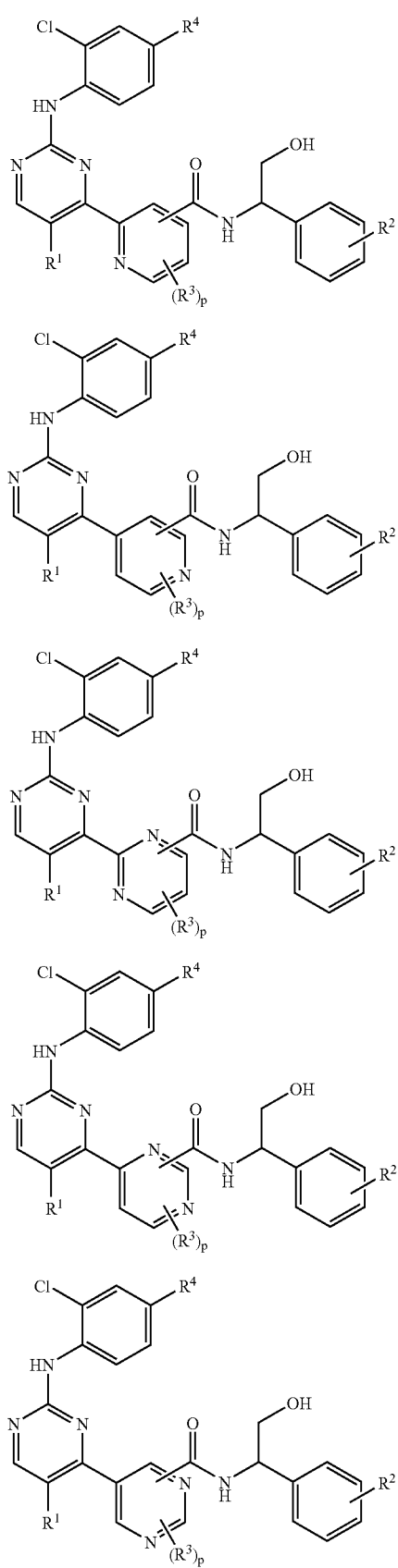
II-cc
II-dd
II-ee
II-ff
II-gg
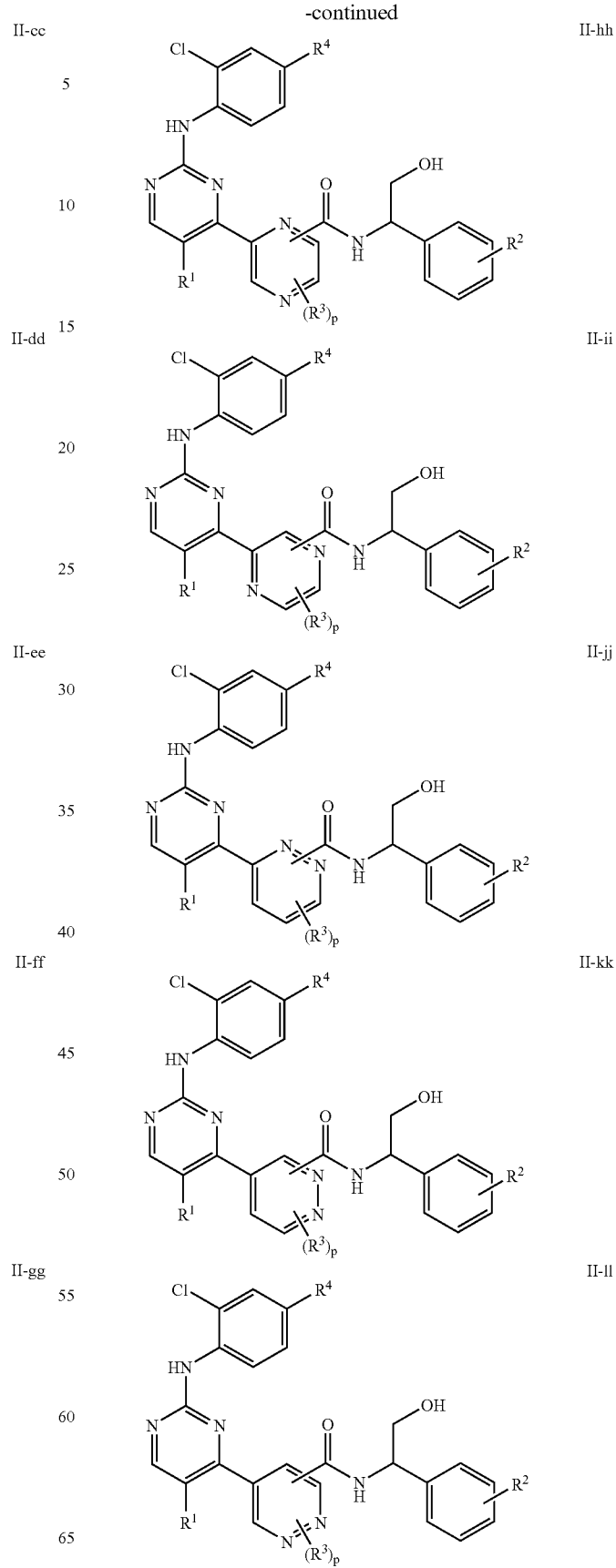
II-hh
II-ii
II-jj
II-kk
II-ll

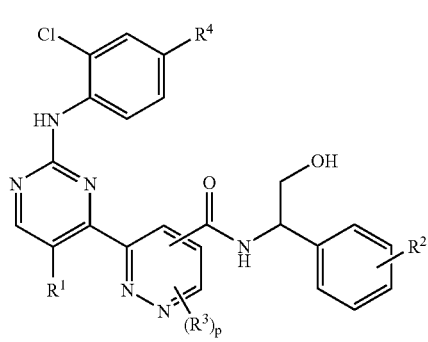
II-mm
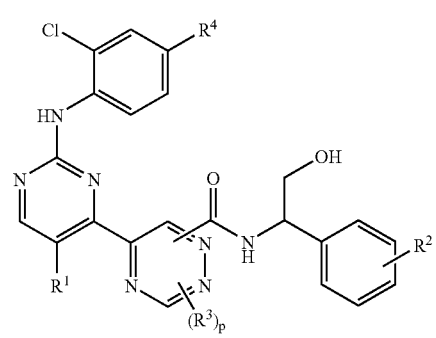
II-nn
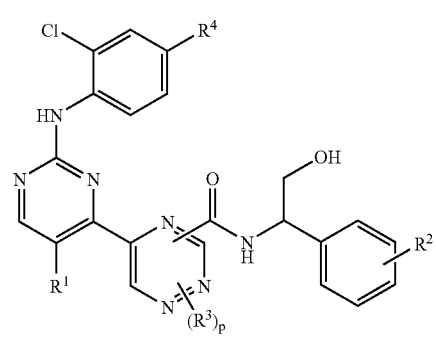
II-oo
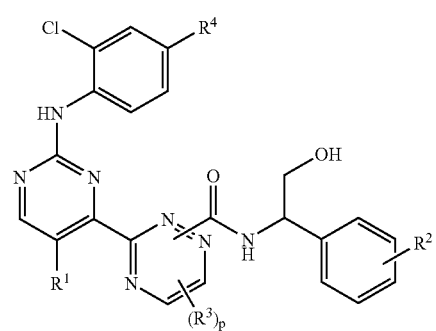
II-pp
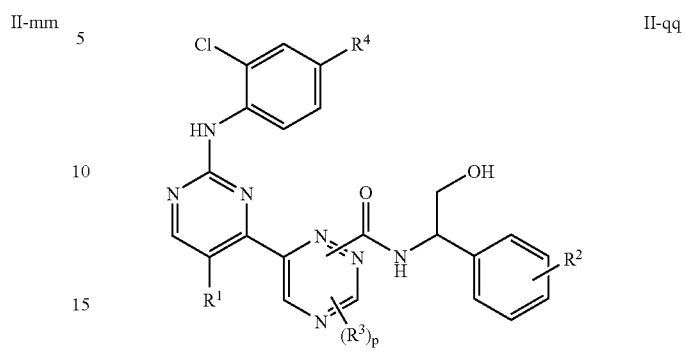
II-qq
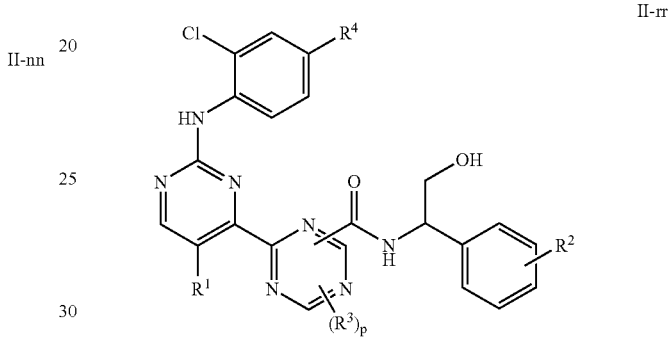
II-rr
Exemplary structures of compounds of formulae I and II are set forth in Table 4.
Table 4. Exemplary Compounds of Formula I
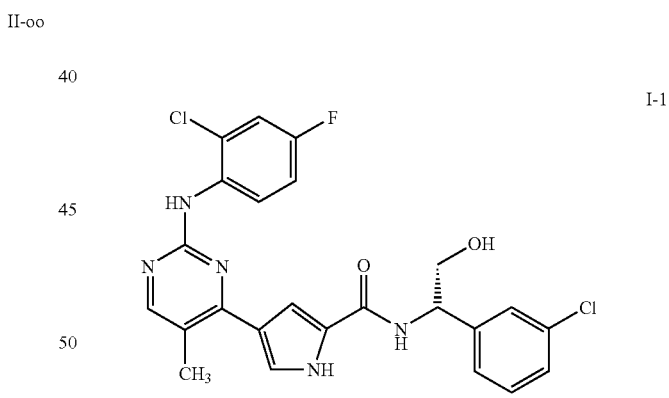
I-1
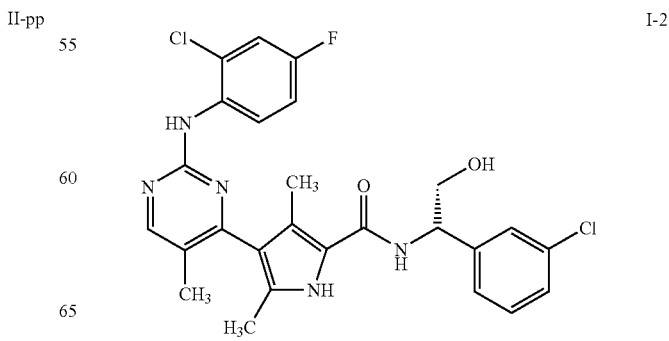
I-2

-continued
I-3
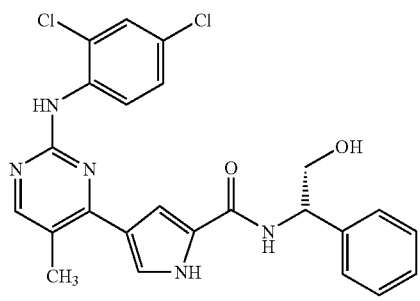
I-4
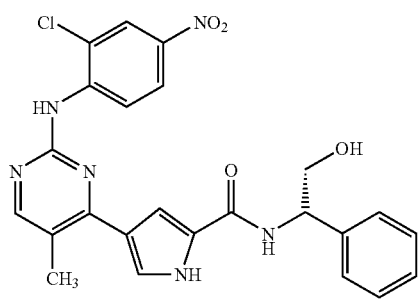
I-5
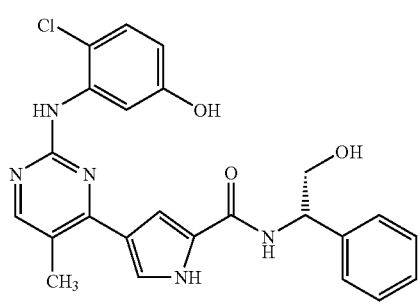
I-6
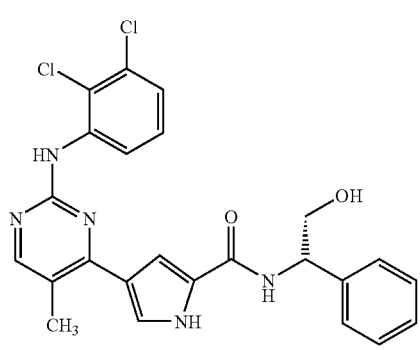
I-7
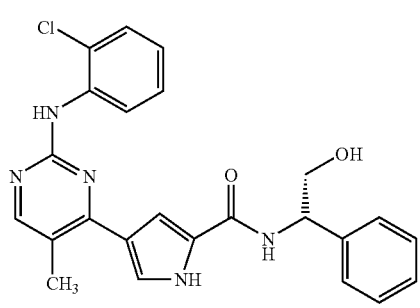
-continued
I-8
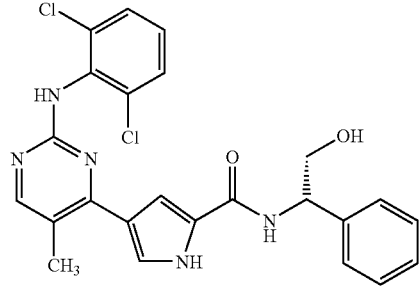
I-9
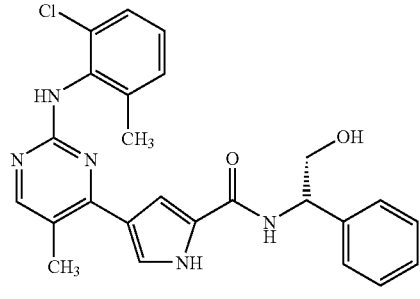
I-10
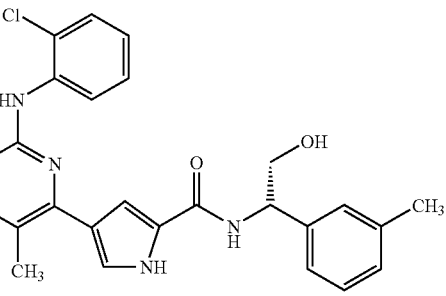
I-11
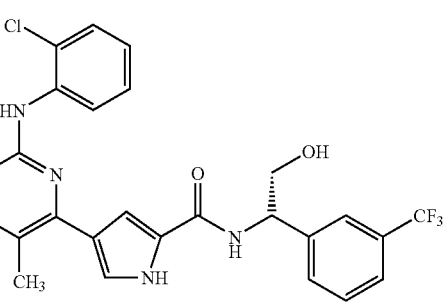
I-12
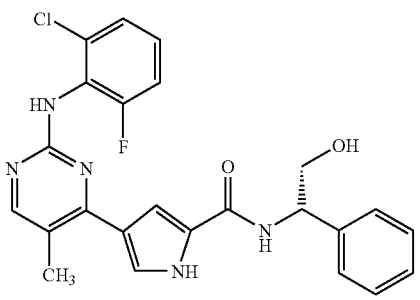
Formulation, Uses, and Administration
The compounds and compositions described herein are generally useful for the inhibition of protein kinase activity of one or more enzymes. In one particular embodiment, the compounds and compositions of the invention are inhibitors of ERK2 and thus the compounds and compositions are particularly useful for treating or lessening the severity of disease or disease symptoms associated with ERK2.

The activity of a compound utilized in this invention as an inhibitor of ERK2 may be assayed in vitro, in vivo or in a cell line. In vitro assays include assays that determine inhibition of either the phosphorylation activity or ATPase activity of activated ERK2. Alternate in vitro assays quantitate the ability of the inhibitor to bind to ERK2. Inhibitor binding may be measured by radiolabeling the inhibitor prior to binding, isolating the inhibitor/ERK2 complex and determining the amount of radiolabel bound. Alternatively, inhibitor binding may be determined by running a competition experiment where new inhibitors are incubated with ERK2 bound to known radioligands. Detailed conditions for assaying a compound utilized in this invention as an inhibitor of ERK2 kinase are set forth in the Examples below.

According to another aspect, the invention features a composition comprising a compound of this invention or a pharmaceutically acceptable derivative thereof and a pharmaceutically acceptable carrier, adjuvant, or vehicle. The amount of compound in the compositions of this invention is such that is effective to detectably inhibit a protein kinase, particularly ERK2, in a biological sample or in a patient. Preferably the composition of this invention is formulated for administration to a patient in need of such composition. Most preferably, the composition of this invention is formulated for oral administration to a patient.

The term "patient," as used herein, means an animal, preferably a mammal, and most preferably a human.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit," as used herein, means a measurable change in ERK2 activity between a sample comprising a compound or composition of the invention and an ERK2 kinase and an equivalent sample comprising ERK2 kinase in the absence of the compound or composition.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of ERK2.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{ alkyl})_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral," as used herein, includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

According to another aspect, the invention features a method of inhibiting protein kinase activity, such as, for example, ERK2 kinase activity, in a biological sample comprising the step of contacting the biological sample with a compound of this invention, or a composition comprising the compound.

The term "biological sample," as used herein, means a sample outside an animal and includes, without limitation, cell cultures or extracts thereof; biopsied material obtained from an animal or extracts thereof; and blood, saliva, urine, feces, semen, tears, or other body fluids or extracts thereof. Inhibition of kinase activity, particularly ERK kinase activity, in a biological sample is useful for a variety of purposes known to one of skill in the art. Examples of such purposes include, but are not limited to, blood transfusion, organ-transplantation, biological specimen storage, and biological assays.

In another aspect, the invention features a method of inhibiting protein kinase activity, such as, for example, ERK2 kinase activity, in a patient comprising the step of administering to the patient a compound of the present invention, or a composition comprising the compound.

According to another embodiment, the invention provides a method for treating or lessening the severity of an ERK2-mediated disease or condition in a patient comprising the step of administering to the patient a composition according to the present invention.

The term "ERK-mediated disease" or "condition," as used herein, means any disease or other deleterious condition in which ERK is known to play a role. Accordingly, another embodiment of the present invention relates to treating or lessening the severity of one or more diseases in which ERK is known to play a role. Specifically, the present invention relates to a method of treating or lessening the severity of a disease or condition selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases, wherein the method comprises administering to a patient in need thereof a composition according to the present invention. In some particular embodiments, the treated disease or condition is cancer. The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include adenocarcinoma; adenoma; adrenocortical cancer; bladder cancer; bone cancer; brain cancer; breast cancer; cancer of the buccal cavity; cervical cancer; colon cancer; colorectal cancer; endometrial or uterine carcinoma; epidermoid carcinoma; esophogeal cancer; eye cancer; follicular carcinoma; gallbladder cancer; gastrointestinal cancer; cancer of the genitourinary tract; glioblastoma; hairy cell carcinoma; various types of head and neck cancer; hepatic carcinoma; hepatocellular cancer; Hodgkin's disease; keratoacanthoma; kidney cancer; large cell carcinoma; cancer of the large intestine; laryngeal cancer; liver cancer; lung cancer, such as, for example, adenocarcinoma of the lung, small-cell lung cancer, squamous carcinoma of the lung, non-small cell lung cancer; melanoma and nonmelanoma skin cancer; lymphoid disorders; myeloproliferative disorders, such as, for example, polycythemia vera, essential thrombocythemia, chronic idiopathic myelofibrosis, myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML, or juvenile myelomonocytic leukemia; neuroblastoma; ovarian cancer; papillary carcinoma; pancreatic cancer; cancer of the peritoneum; prostate cancer, including benign prostatic hyperplasia; rectal cancer; salivary gland carcinoma; sarcoma; seminoma; squamous cell cancer; small cell carcinoma; cancer of the small intestine; stomach cancer; testicular cancer; thyroid cancer; undifferentiated carcinoma; and vulval cancer. In particular embodiments, the treated cancer is melanoma, breast cancer, colon cancer, or pancreatic cancer.

The treatment method that includes administering an ERK inhibitor of the invention can further include administering to the patient an additional therapeutic agent (combination therapy) selected from: a chemotherapeutic or anti-proliferative agent, or an anti-inflammatory agent, wherein the additional therapeutic agent is appropriate for the disease being treated and the additional therapeutic agent is administered together with a compound or composition of the invention as a single dosage form or separately from the compound or composition as part of a multiple dosage form. The additional therapeutic agent may be administered at the same time as a compound of the invention or at a different time. In the latter case, administration in normally within 5 hours or each other but may be staggered by, for example, 6 hours, 12 hours, 1 day, 2 days, 3 days, 1 week, 2 weeks, 3 weeks, 1 month, or 2 months. Non-limiting examples of chemotherapeutic agents or other anti-proliferative agents that may be combined with the compounds of this invention include adriamycin, gemcitabine, cyclophosphamide, dexamethasone, etoposide, fluorouracil, Gleevec™, interferons, platinum derivatives, such as carboplatin, topotecan, taxol, vinblastine, and vincristine.

The amount of compound of the invention or the amount of compound and additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01-100 mg/kg body weight/day of a compound of formula I can be administered.

In those compositions that include an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention.

Preparation of the Compounds of the Invention

The compounds of the present invention may be prepared according to methods known to one or ordinary skill in the art and by those described in U.S. Pat. No. 6,743,791, the entirety of which is hereby incorporated by reference. Scheme 1 shows a general synthetic route that is used for preparing the pyrrol-3-yl compounds of formula I-tt of this invention.

Accordingly, propanoyl chloride is combined with 2,2,2-trichloro-1-(1H-pyrrol-2-yl)ethanone, dichloromethane, and aluminum trichloride to form compound 101. N—((S)-2-hydroxy-1-phenylethyl)-4-propionyl-1H-pyrrole-2-carboxamide (compound 102) is formed by treating compound 101 with (S)-2-amino-2-phenylethanol in DMF at ambient temperature. 4-((Z)-3-(dimethylamino)-2-methylacryloyl)-N—((S)-2-hydroxy-1-phenylethyl)-1H-pyrrole-2-carboxamide (compound 103) is formed by treating compound 102 with tert-butoxy-N,N,N',N'-tetramethylmethanediamine at ambient temperature. The formation of a compound of formula I-tt, where $R^4$ is as defined herein, is achieved by the treatment of compound 103 with a guanidine of formula I-ss at elevated temperature, such as, for example, refluxing ethanol. Alternatively, compound 103 may be treated with S-methyl thiourea to produce N—((S)-2-hydroxy-1-phenylethyl)-4-(5- methyl-2-(methylthio)pyrimidin-4-yl)-1H-pyrrole-2-carboxamide, which may in turn be oxidized with m-CPBA to the corresponding sulfone. The sulfonyl group may be subsequently displaced by an aniline corresponding to the phenylguanidine of formula I-ss to generate a compound of formula I-tt. The compounds of formula III-a synthesized by this method, as exemplified in Table 1, were isolated by preparatory HPLC (reversed-phase, 10 to 90% CH₃CN in water over 15 minutes).

be appreciated that other compounds of the present invention are prepared in accordance with the teachings provided herein and with methods known to one or ordinary skill in the art. Each $^1$H—NMR was obtained at 500 MHz.

The following definitions describe terms and abbreviations used herein:
ATP adenosine triphosphate
DCM dichloromethane
DMF dimethylformamide

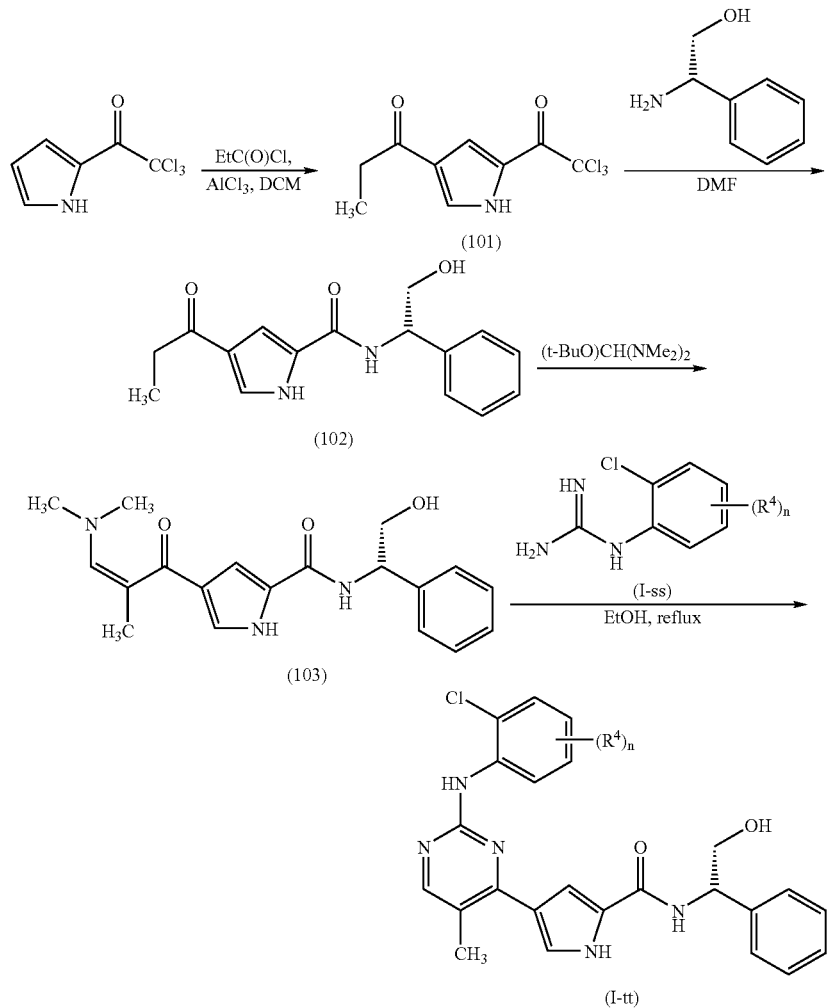

Although certain exemplary embodiments are depicted and described herein, it will be appreciated that compounds of the invention can be prepared as generally described herein using appropriate starting materials that are commercially available or obtained by methods generally available to one of ordinary skill in the art. In order that the invention described herein may be more fully understood, the following examples are set forth. It should be understood that these examples are for illustrative purposes only and are not to be construed as limiting this invention in any manner.

EXAMPLES

The following examples provide detailed methods for preparing exemplary compounds of the present invention. It will EDCI 1-ethyl-3-(3-dimethyaminopropyl)carbodiimide
ESMS electrospray mass spectrometry
HEPES 4-(2-hydroxyethyl)-1-piperazineethanesulfonic acid
HOBt 1-Hydroxy-1H-benzotriazole
HPLC high performance liquid chromatography
LC-MS liquid chromatography-mass spectrometry
Me methyl
MeOH methanol
NADH nicotinamide adenine dinucleotide hydride
Ph phenyl
tBu tertiary butyl
TLC thin layer chromatography
TFA trifluoacetic acid
THF tetrahydrofuran

Example 1

4-[2-(2-Chloro-4-fluoro-phenylamino)-5-methyl-pyrimidin-4-yl]-1H-pyrrole-2-carboxylic acid [1-(3-chloro-phenyl)-2-hydroxy-ethyl]-amide (I-1)

Compound 103 was prepared as indicated in Scheme 1. This compound was treated with (2-chloro-4-fluorophenyl) guanidine in refluxing ethanol for 12 hours. The volatiles were removed under reduced pressure and the resulting crude compound I-1 was purified by reversed-phase HPLC; $^1$H—NMR (methanol-$d_4$): δ 7.2-8.15 (m, 10H), 5.2 (m, 1H), 3.85 (m, 2H), 2.5 (s, 3H). Treatment of compound 103 with (2,4-dichlorophenyl)guanidine and (2-chloro-4-nitrophenyl) guanidine provided compounds I-3; $^1$H—NMR (methanol-$d_4$): δ 2.45 (s, 3H), 3.8 (broad d, 2H), 5.1 (t, 1H), 7.3 (t, 1H), 7.35 (t, 2H), 7.4 (m, 3H), 7.6 (s, 1H), 7.65 (s, 1H), 7.8 (s, 1H), 8.1 (d, 1H), 8.2 (s, 1H), and I-4; $^1$H—NMR (methanol-$d_4$): δ 2.5 (s, 3H), 3.8 (d, 2H), 5.2 (t, 1H), 7.2 (m, 1H), 7.3 (m, 2H), 7.4 (s, 1H), 7.7 (d, 2H), 8.2 (d, 1H), 8.3 (s, 2H), 9 (d, 1H), respectively.

Example 2

4-[2-(2-Chloro-4-fluoro-phenylamino)-5-methyl-pyrimidin-4-yl]-3,5-dimethyl-1H-pyrrole-2-carboxylic Acid [1-(3-chloro-phenyl)-2-hydroxy-ethyl]-amide (I-2)

The same procedure used in the synthesis of compound 103 was followed, substituting 2,2,2-trichloro-1-(3,5-dimethyl-1H-pyrrol-2-yl)ethanone for 2,2,2-trichloro-1-(1H-pyrrol-2-yl)ethanone to produce 4-((Z)-3-(dimethylamino)-2-methylacryloyl)-N—((S)-2-hydroxy-1-phenylethyl)-3,5-dimethyl-1H-pyrrole-2-carboxamide. This compound was treated with (2-chloro-4-fluorophenyl)guanidine in refluxing ethanol for 12 hours. The volatiles were removed under reduced pressure and the resulting crude compound I-2 was purified by reversed-phase HPLC; $^1$H—NMR (methanol-$d_4$): δ 8.2 (d, 1H), 7.75 (m, 1H), 7.1-7.4 (m, 7H), 5.1 (m, 1H), 3.8 (m, 2H), 2.45 (s, 3H), 2.35 (s, 3H).

Example 3

ERK2 Inhibition Assay

Compounds were assayed for the inhibition of ERK2 by a spectrophotometric coupled-enzyme assay (Fox et al *Protein Sci.* 1998, 7, 2249). In this assay, a fixed concentration of activated ERK2 (10 nM) was incubated with various concentrations of a compound of the present invention in DMSO (2.5%) for 10 min. at 30° C. in 0.1 M HEPES buffer (pH 7.5), containing 10 mM MgCl$_2$, 2.5 mM phosphoenolpyruvate, 200 μM NADH, 150 μg/ml pyruvate kinase, 50 μg/ml lactate dehydrogenase, and 200 μM erktide peptide. The reaction was initiated by the addition of 65 μM ATP. The rate of decrease of absorbance at 340 nM was monitored. The $K_i$ values were determined from the rate data as a function of inhibitor concentration and are presented in Table 5, where a $K_i$ of less than or equal to 0.1 μM is designated "A" and a $K_i$ of greater than 0.1 μM is designated "B." The compound numbers in Table 5 correspond to the compound numbers in Table 4.

TABLE 5

| Compound No. | ERK2 Ki (μM) |
|---|---|
| I-1 | A |
| I-3 | A |
| I-4 | A |
| I-6 | A |
| I-8 | B |
| I-9 | B |
| I-10 | A |
| I-11 | A |
| I-12 | A |

Example 4

ERK2 Inhibition: Cell Proliferation Assay

Compounds may be assayed for the inhibition of ERK2 by a cell proliferation assay. In this assay, a complete media is prepared by adding 10% fetal bovine serum and penicillin/streptomycin solution to RPMI 1640 medium (JRH Biosciences). Colon cancer cells (HT-29 cell line) are added to each of 84 wells of a 96 well plate at a seeding density of 10,000 cells/well/150 μL. The cells are allowed to attach to the plate by incubating at 37° C. for 2 hours. A solution of test compound is prepared in complete media by serial dilution to obtain the following concentrations: 20 μM, 6.7 μM, 2.2 μM, 0.74 μM, 0.25 μM, and 0.08 μM. The test compound solution (50 μL) is added to each of 72 cell-containing wells. To the 12 remaining cell-containing wells, only complete media (200 μL) is added to form a control group in order to measure maximal proliferation. To the remaining 12 empty wells, complete media is added to form a vehicle control group in order to measure background. The plates are incubated at 37° C. for 3 days. A stock solution of $^3$H-thymidine (1 mCi/mL, New England Nuclear, Boston, Mass.) is diluted to 20 μCi/mL in RPMI medium then 20 μL of this solution is added to each well. The plates are further incubated at 37° C. for 8 hours then harvested and analyzed for $^3$H-thymidine uptake using a liquid scintillation counter.

Example 5

ERK1 Inhibition Assay

Compounds are assayed for the inhibition of ERK1 by a spectrophotometric coupled-enzyme assay (Fox et al (1998) *Protein Sci* 7, 2249). In this assay, a fixed concentration of activated ERK1 (20 nM) is incubated with various concentrations of the compound in DMSO (2.0%) for 10 minutes at 30° C. in 0.1 M HEPES buffer, pH 7.6, containing 10 mM MgCl$_2$, 2.5 mM phosphoenolpyruvate, 200 μM NADH, 30 μg/mL pyruvate kinase, 10 μg/mL lactate dehydrogenase, and 150 μM erktide peptide. The reaction is initiated by the addition of 140 μM ATP (20 μL). The rate of decrease of absorbance at 340 nM is monitored. The $K_i$ is evaluated from the rate data as a function of inhibitor concentration.

All publications and patents cited in this specification are herein incorporated by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

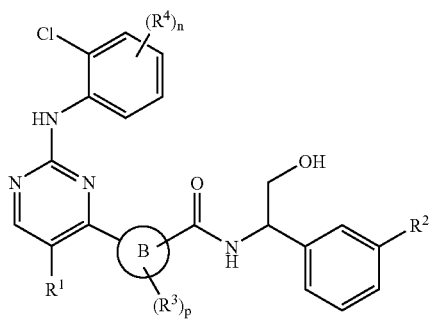

or a pharmaceutically acceptable salt thereof, wherein:
R$^1$ is CH$_3$;
each R is independently selected from hydrogen or a C$_{1-6}$ aliphatic group;
R$^2$ is R or halogen;
p is 0; and
R$^4$ is selected from NO$_2$, R, F, or Cl.

2. The compound according to claim 1, wherein R$^2$ is chloro.

3. The compound according to claim 1, wherein R$^2$ is hydrogen.

4. The compound according to claim 1, wherein R$^4$ is fluoro or NO$_2$.

5. The compound selected from the group consisting of:

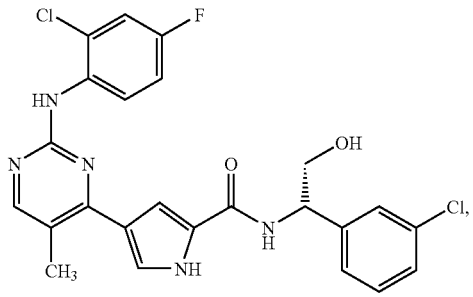

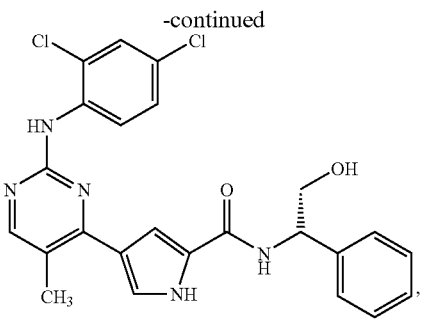

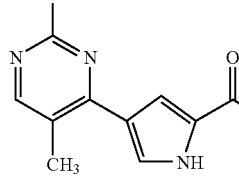

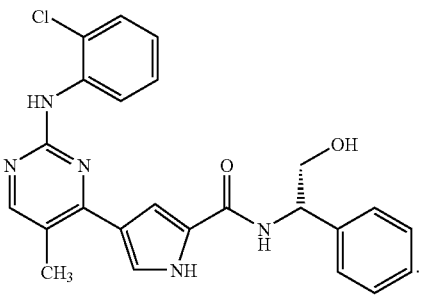

6. A composition comprising a compound according to claim 1 and a pharmaceutically acceptable carrier, adjuvant, or vehicle.

7. A method of treating or lessening the severity of colon cancer comprising the step of administering to a patient in need thereof a composition according to claim 6.

* * * * *